United States Patent [19]

Anderson

[11] Patent Number: 4,696,300

[45] Date of Patent: Sep. 29, 1987

[54] FASTENER FOR JOINING MATERIALS

[75] Inventor: Gary Anderson, Dorchester, Mass.

[73] Assignee: Dennison Manufacturing Company, Framingham, Mass.

[21] Appl. No.: 722,083

[22] Filed: Apr. 11, 1985

[51] Int. Cl.[4] .............................................. A61B 17/04
[52] U.S. Cl. .............................. 128/334 R; 411/458;
273/DIG. 5; 273/DIG. 6; 273/DIG. 8
[58] Field of Search ...................... 128/334 R, 334 C;
411/458, 459, 460, 457, 446, 447; 227/19

[56] References Cited

U.S. PATENT DOCUMENTS 3,875,648  4/1975  Bone ...................................... 227/19
4,490,326  12/1984  Beroff et al. ..................... 128/334 R
4,513,746  4/1985  Aranyi et al. ................... 128/334 C

FOREIGN PATENT DOCUMENTS 129442  12/1984  European Pat. Off. ........ 128/334 C
284898  3/1928  United Kingdom ................ 411/460

Primary Examiner—Richard C. Pinkham
Assistant Examiner—G. Jackson
Attorney, Agent, or Firm—Gary S. Winer

[57] ABSTRACT

A fastener comprises a filament having two opposing heads. The heads have two ends defining non-parallel planes, forming acute angles which share a common ray. The fastener is installed by being driven through two needles having slotted bores.

15 Claims, 21 Drawing Figures

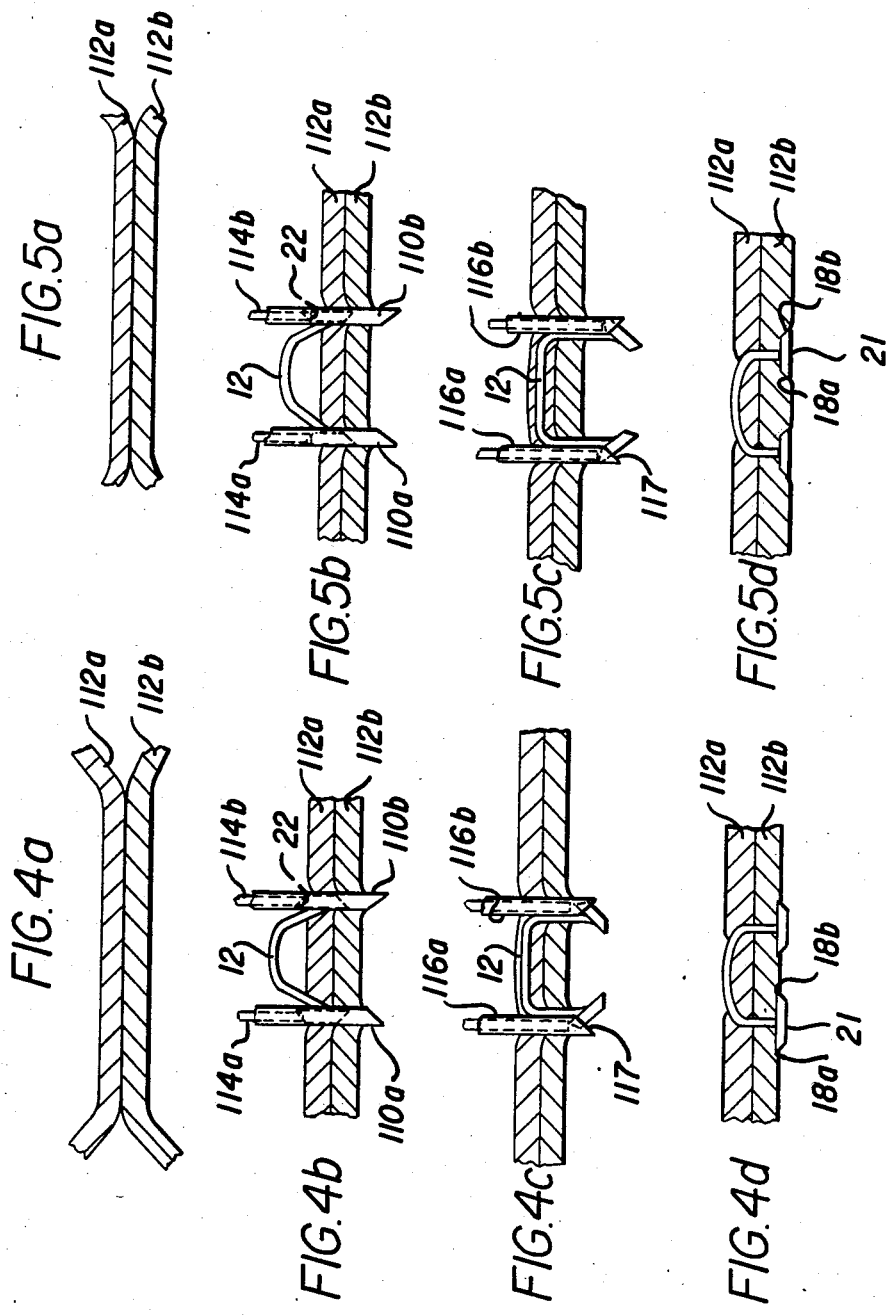

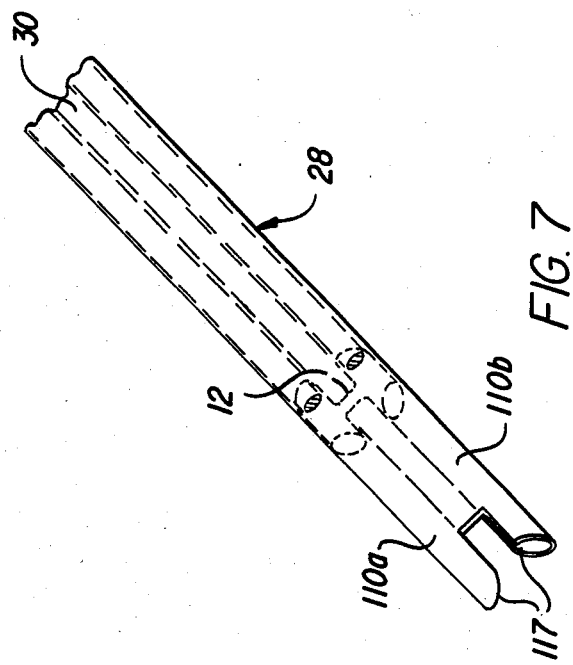

FASTENER FOR JOINING MATERIALS

BACKGROUND OF THE INVENTION

This invention relates to fastening, and more particularly to methods and apparatus for the fastening of biological tissues.

A method of joining biological tissue is shown in U.S. Pat. No. 3,086,208. A U-shaped clip having barbs is applied to folded tissue layers, as for the closing of incisions. A feature of the installed clip is that it juts out from the joined area. This can be disadvantageous for fastening internal tissues because the clip could extend into interstitial areas between the fastened tissue and adjacent tissues. Thus irritation can occur, or the clip can be worked loose causing evisceration. Moreover, numerous clips must be employed for high strength fastening, due to the small area over which force is applied.

Another fastener used in joining tissues has the form of an adhesive strip. The strip extends across an incision, thus holding the wound closed. A limitation of this device is that it is not appropriate for the fastening of internal structures. Further, the fastener lacks sufficient strength for high stress applications.

One of the most common tissue fasteners are thread sutures. These fasteners are installed by sewing the suture through the structures to be fastened. A disadvantage to sutures lies in the relatively great amount of time required for installation. Installation delays result in high operating room costs and increased patient trauma. Moreover, while these sutures may be installed in biodegradable (dissolvable) form, they dissolve fairly rapidly, making their use unsuitable in applications where fastening strength must be maintained over longer time periods.

Thus, it is an object of the invention to provide a fastener which is rapidly installed and which renders high initial levels of fastening strength. (tensile strength)

It is an additional object to provide a fastener and installation apparatus which may be used for internal application, without requiring extensive surgery.

It is a further object of the invention to provide a fastener which is biodegradable, yet maintains high fastening strength over a relatively longer time period than known fasteners.

It is yet another object of the invention to provide a fastener which becomes firmly anchored in the fastened structures and avoids protuberances into neighboring interstitial areas.

SUMMARY OF THE INVENTION

In accordance with the invention, the fastener comprises a connecting member and two opposing heads having non-coplanar ends, that is, ends defining non-parallel planes. The head ends have acute angles which share a common ray, thus forming opposing pointed ends. The heads may be provided with a variety of cross-sectional configurations, while in a preferred embodiment, the heads have a cylindrical cross-section, and are trapeziform or trapezoidal in shape.

In accordance with one embodiment of the invention, the fasteners are installed by being driven through needles having slotted bores. The needles pierce the layers to be fastened, and the heads are urged down the needle bores via rods. In one embodiment, the heads are provided with a flattened profile to receive securely the rod end.

According to another aspect of the invention, the fasteners are used to join resilient or conformable layers. The heads are drawn into the conformable layers, whereupon the opposing pointed ends become embedded therein. Thus, protuberance is minimized, and the head is more securely positioned.

In accordance with a further aspect of the invention, fasteners according to the invention are used to join biological tissues, as in medical applications. Of particular advantage is the embedment of the opposing pointed ends in the fastened tissue, wherein irritation through contact with adjacent structure is minimized. Further, the fasteners may be fabricated from biodegradable materials, thus allowing for natural healing. Due to the relatively high mass of the fastener, as compared to common sutures, loss of fastening strength through degradation is delayed.

In accordance with yet another aspect of the invention, the fastener is installed with elongated needles, stabilized by a channel through which the connector passes. An arthroscope may be used in conjunction with the elongated needles for purposes of non-invasive surgical fastening.

BRIEF DESCRIPTION OF THE DRAWINGS

Other aspects of the invention will become apparent after considering several illustrative embodiments taken in conjunction with the drawings in which:

FIGS. 4a-4d schematic views of a sequence of operations in installing the fastener shown in FIG. 2a;

FIGS. 5a-5d are schematic views of a sequence of operations in installing the fastener shown in FIG. 2b;

FIG. 7 is a perspective view of a fastener installation apparatus in accordance with the invention.

DETAILED DESCRIPTION OF THE INVENTION

With reference to FIGS. 1-7, the invention provides for the fastening of layers of material, wherein the fastener 10 has two opposing heads 14a, 14b having pointed ends which are embedded in the material when installed.

Figure 1:
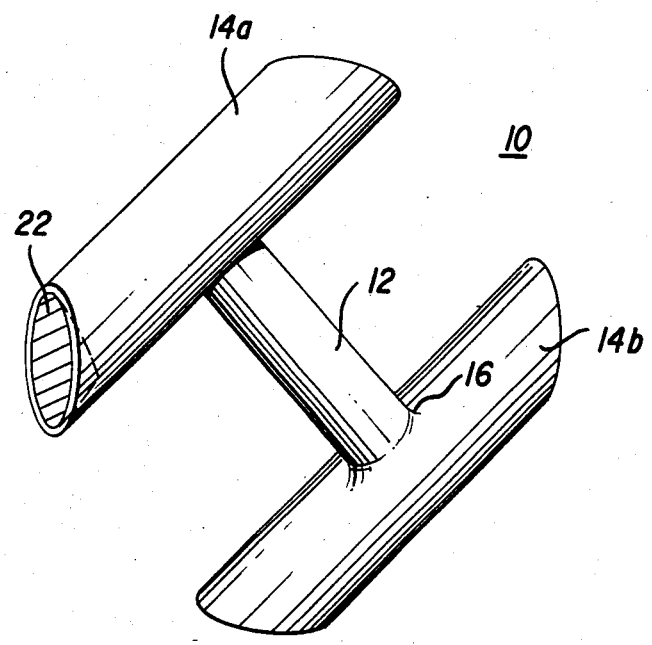
FIG. 1 is a perspective view of a fastener in accordance with the invention.
Figure 3A:
FIGS. 3a-3f are cross sectional views taken along line 3A—3A on FIG. 2, showing various head configurations.
Figure 3B:
Figure 3C:
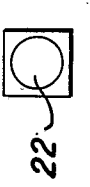
Figure 3D:
Figure 3E:
Figure 3F:

FIG. 1 shows a preferred embodiment of the invention, which comprises a connecting member 12, which may be bar shaped, coupled to two heads 14a, 14b. The fastener is integrally fabricated, as in a mold, with a radial expansion 16 between connecting bar 12 and heads 14a, 14b.

Figure 2A:
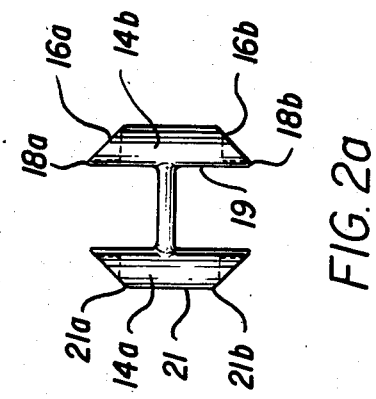
FIGS. 2a and 2b and plan views of two embodiments of fasteners of the invention.
Figure 2B:
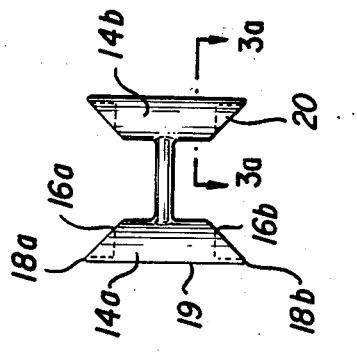

With reference to FIG. 2, it can be seen that heads 14a, 14b are provided with a plurality of ends, preferably two, defining non-parallel planes, 16a, 16b having acute angles 18a, 18b which share a common ray 19. In FIG. 2a, angles 18a, 18b are disposed closest to the connecting bar 12, while in FIG. 2b, they are furthest away from connecting bar 12. Thus, the heads may be trapeziform, or trapezoidal in shape. Various cross-sectional shapes are shown in FIGS. 3 (a-f), taken along line 3A—3A of FIG. 2.

With reference to FIGS. 4 and 5, the fastener 10 of the invention may be installed by driving heads 14a, 14b through needles 110a, 110b having a slotted bore. Connecting bar 12 extends through slots 116a, 116b. Needles 110a, 110b have sharpened ends which pierce through layers 112a, 112b, whereupon rods 114a, 114b urge heads 14a, 14b down the needle bore. For proper rod/head contact, heads 14a, 14b may be provided with recesses 20 (FIG. 2) sized to securely engage the rod end. As heads 14a, 14b emerge from needles 110a, 110b, the heads toggle in the direction of the opened needle profile 117. After rods 114a, 114b have driven heads 14a, 14b completely out of the needle bore, the needles are withdrawn. Heads 14a, 14b lie flat against layer 112b, and are drawn inwards by a resilient force exerted via connecting bar 12, and through pressure exerted by the joined layers.

The fasteners of the present invention are advantageously employed in the joining of a plurality of layers, where the layer facing installed heads 14a, 14b is resilient or conformable. The fasteners can thus be employed to avoid protuberances at the joined area. If layer 112b is rubber, for example, heads 14a, 14b are drawn inwardly into layer 112b. Heads 14a, 14b are more securely anchored by points 18a, 18b, which become embedded within the layer material.

The fasteners of the present invention are particularly useful in medical applications, where it is desired to fasten biological structures such as layers of tissue, cartilage, and or bone. As shown in FIGS. 4 (d) and 5 (d), points 18a and 18b are embedded in tissue layers, 112b. A countersinking effect is realized, wherein the fastener heads 14a, 14b are partially (FIG. 4(d)) or wholly (FIG. 5(d)) disposed within layer 112b. In surgical applications, exposed sharp edges may cause irritation, particularly where other tissue layers contact the heads 14a, 14b. To minimize protuberances, therefore, the profile may be provided with rounded edges 21a, 21b.

Figure 6B:
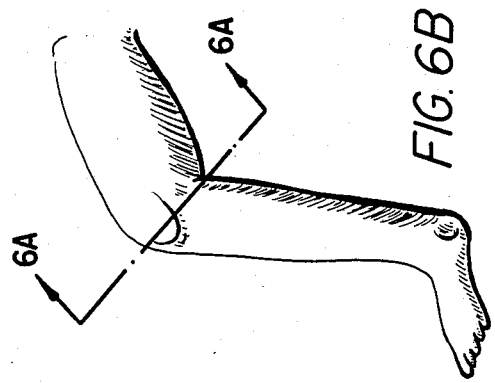
FIG. 6A is a cross-sectional view of a knee joint taken along line 6A—6A of FIG. 6B, showing a fastener in accordance with the invention fastening a tear in the medial meniscus.
Figure 6A:
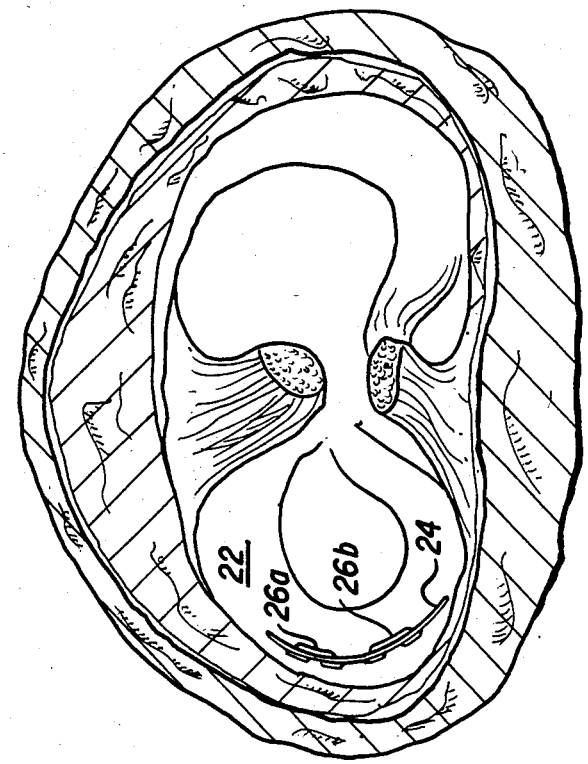

An illustrative surgical application is shown in FIG. 6, depicting the medial and lateral meniscus of the knee, in cross section taken along line 6A—6A of FIG. 6B. The medial meniscus 22 has been torn. The tear 24 is shown repaired with fasteners 26a, 26b. The tear edges may be considered as layers 112a, 112b of FIG. 4. Arthroscopy may be employed in combination with elongated installation needles 28, such as are shown in FIG. 7. The needles are formed from a tube, longitudinally compressed to form a channel 30, through which connecting bar 12 may pass. Channel 30 additionally serves to rigidize the elongated needles, and to maintain same in proper spaced relationship.

The fasteners may be fabricated from elastomers or plastics, including polyurethane, polyvinylchloride and NYLON (a polyamide polymer) and its derivatives, including nylon 66. For surgical applications, a biodegradable material may be used, wherein the fasteners are fabricated from materials including: Polylactic acids (and its isomers); polyglycolic acid; polydioxanone; or polyglactin. Due to the greater mass of the fasteners of the invention, as compared to common thread sutures, biodegradation can be extended over a longer time period. Hence, where the fastened tissues are poorly vascularized, fastening strength can be maintained over a longer time period, thus enabling the use of biodegradable materials in a wider range of applications.

The fasteners of the present invention may be of greatly varying size, depending on the particular use to which they will be applied. Typically, the length of connecting bar 12 is in the range of 5.0 to 80.0 mm. Typical head and connecting bar thickness ranges from 0.3–3.0 mm. It should be understood, however, that size may vary far beyond these ranges.

Figure 8:
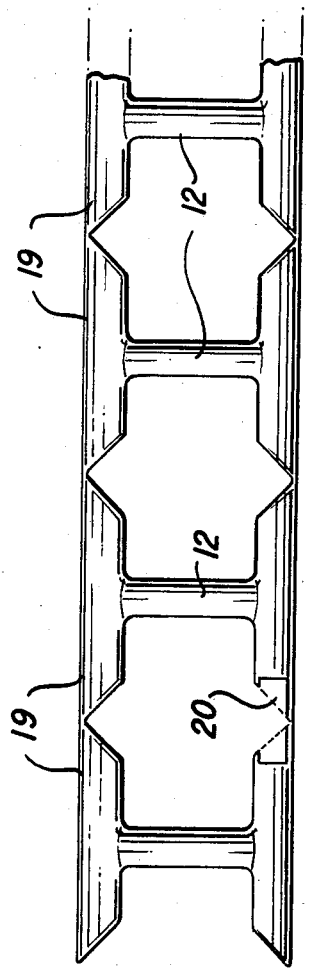
FIG. 8 is a plan view of an assemblage of fasteners of the type shown in FIG. 2b.

Fasteners, according to the invention, may be provided as continuously molded stock, or in assemblages of connected fasteners, for example assemblages of ten fasteners. FIG. 8 illustrates the fastener of FIG. 2A connected at points 18a and 18b. The installation apparatus severs the individual fasteners prior to installation, as described, for example, in U.S. Pat. No. 4,039,078.

Additionally, fasteners, according to the invention, may be stretched to reorient the molecular structure of connecting bar 12, thus providing greater levels of tensile strength. Stretching may be performed during the fastener manufacturing process either in-mold or out of mold, with the introduction of external heat or without, as the particular application requires.

While various aspects of the invention have been set forth by the drawings and the specification, it is to be understood that the foregoing detailed description is for illustration only and that various changes in parts, as well as the substitution of equivalent constituents for those shown and described, may be made without departing from the spirit and scope of the invention as set forth in the appended claims.

What is claimed is:
1. Apparatus for fastening materials, comprising:
   a connecting member having at least two ends;
   a plurality of head members, one connected to each of said ends, with each head having at least two ends defining non-parallel planes; and
   means for driving said heads through needles having slotted bores;
   wherein said head ends are provided with apertures disposed to securely receive the driving means.
2. Apparatus of claim 1, wherein said heads define a trapezium.
3. Apparatus of claim 1, wherein said heads define a trapezoid.
4. Apparatus of claim 1, wherein said connecting member ends extend radially outwards to form said head members.
5. Apparatus of claim 1, wherein said connecting member is a stretched filament.
6. Apparatus of claim 1, wherein said head member ends define acute angles of less than 60 degrees.
7. Apparatus of claim 6, wherein said apparatus are connected via a narrow filament extending between said acute angles, thus forming an assemblage.
8. Apparatus of claim 1, wherein said head member ends define acute angles sharing a common ray.
9. Apparatus of claim 1, wherein said connecting member and head-members are integrally formed.
10. Apparatus of claim 9, wherein said apparatus is plastic.
11. Apparatus of claim 9, wherein said apparatus is polylactic acid or its isomers.
12. Apparatus of claim 9, wherein said apparatus is biodegradable.
13. Apparatus of claim 1, wherein individual ones of said apparatus are connected to form an assemblage.
14. Apparatus of claim 1, wherein said connecting member is between 0.1 and 2 mm in thickness, and 3 to 30 mm in length.
15. Apparatus of claim 1, wherein said heads are between 0.1 and 2 mm in thickness and 2 to 10 mm in length.

* * * * *